United States Patent [19]

Heinecke

[11] Patent Number: 5,731,208
[45] Date of Patent: Mar. 24, 1998

[54] METHOD OF DETECTING CONDITIONS INDICATIVE OF ATHEROSCLEROSIS

[75] Inventor: Jay W. Heinecke, St. Louis, Mo.

[73] Assignee: Washington University, St. Louis, Mo.

[21] Appl. No.: 709,700

[22] Filed: Sep. 9, 1996

[51] Int. Cl.$^6$ ................................................. G01N 33/48
[52] U.S. Cl. ................................. 436/86; 436/89; 436/811
[58] Field of Search ............................ 436/86, 89, 155, 436/161, 174, 811

[56] References Cited

PUBLICATIONS

Berliner and Heinecke, *Free Radical Biol. & Med.*, vol. 20, pp. 707–727 (1996).
Daugherty et al., *J. Clin. Invest.*, vol. 94, pp. 437–444 (1994).
Heinecke et al., *J. Biol. Chem.*, vol. 268, pp. 4069–4077 (1993).
Heinecke et al., *J. Clin. Invest.*, vol. 91, pp. 2866–2872 (1993).
Hazen et al., *J. Biol. Chem.*, vol. 271, pp. 1861–1867 (1996).
Heinecke et al., *Biochemistry*, vol. 33, pp. 10127–10136 (1994).
Savenkova et al., *J. Biol. Chem.*, vol. 269, pp. 20394–20400 (1994).
Hazen et al., *J. Clin. Invest.*, vol. 98, No. 6, pp. 1283–1289 (1996).
Hazen et al., *J. Biol. Chem.*, vol. 271, No. 38, pp. 23080–23088 (1996).
Heinecke et al., *J. Clin. Invest.* vol. 77, pp. 757–761 (1986).

*Primary Examiner*—Lyle A. Alexander
*Attorney, Agent, or Firm*—Scott J. Meyer

[57] ABSTRACT

A diagnostic method and screening test for atherosclerosis and analogous diseases involving activated phagocytes and/or inflammation is provided which comprises determining the presence of p-hydroxyphenylacetaldehyde-lysine in a test sample of a body fluid or tissue at a level which is elevated relative to the level in a normal patient.

5 Claims, 9 Drawing Sheets

METHOD OF DETECTING CONDITIONS INDICATIVE OF ATHEROSCLEROSIS

This invention was made in part with government support under grant number AG 12293 awarded by the National Institutes of Health. The government has certain rights in the invention.

BACKGROUND OF THE INVENTION

This invention relates to a novel diagnostic method. More particularly, the invention is directed to a diagnostic method and screening test for atherosclerosis and analogous diseases involving activated phagocytes and/or inflammation such as, for example, arthritis, inflammatory bowel disease, ischemia-reperfusion injury and the like inflammatory and vascular diseases.

A leading cause of death in the United States is heart disease. About one million persons in the U.S. die of heart disease annually. Heart disease is actually a wide variety of diseases. The principal cause of many of them is atherosclerosis.

Atherosclerosis is a common form of arteriosclerosis in which fatty deposits, referred to as plaques, build up within the intima (inner wall of the arteries). As a consequence of the resulting narrowing on the arteries that feed blood to the heart, the heart's supply of oxygen, which is carried by the blood, is reduced. When blood supply is diminished appreciably, the individual may feel the pain of angina pectoris. Such pain is frequently exacerbated when the heart requires an unusually large amount of blood, e.g., during emotional stress or exercise. When the heart is thus deprived of its oxygen supply, heart muscle tissue dies. That is, a coronary occlusion or myocardial infarction may result, which can be fatal if a large area of tissue is affected.

Therefore, when an individual experiences the symptoms of angina pain, prompt contact with medical help is advised. Quick medical attention may be necessary to prevent a myocardial infarction or to provide therapeutic intervention if it has already occurred.

Although there are numerous therapeutic agents which have been used for combating heart disease, their use may be limited in instances where excessive tissue damage has already occurred. Surgical intervention such as angioplasty or bypass surgery may be indicated.

In view of the foregoing, it is apparent that a diagnostic method and screening test for atherosclerosis would have significant practical use in the medical field. Such a diagnostic would be useful for instituting precautionary measures within the individual's control, such as diet, exercise, etc., or administering therapeutic intervention before the onset of a myocardial infarction.

Accordingly, it is a principal object of the present invention to provide a diagnostic method or preventive screening test for atherosclerosis and analogous diseases involving activated phagocytes and/or inflammation such as, for example, arthritis, inflammatory bowel disease, ischemia-reperfusion injury and the like inflammatory and vascular diseases.

It is a further object to provide a diagnostic method for atherosclerosis which preferably is essentially non-invasive to the patient, as distinguished from invasive procedures such as, for example, cardiac catheterization.

(Note: Literature references on the following background information and conventional test methods and laboratory procedures well-known to the person skilled in the art, and other such state-of-the-art techniques as used herein, are indicated in parentheses, and appended at the end of the specification.)

Hypercholesterolemia and hyperglycemia are two important risk factors for atherosclerotic vascular disease (1,2).

The covalent modification of proteins by reactive aldehydes has been implicated in atherogenesis in both of these disorders (3–5). Previous reports indicate that low density lipoprotein (LDL), the major carrier of blood cholesterol, must be oxidatively modified to trigger the pathological events of atherosclerosis (4,6,7).

Aldehydes derived from oxidized LDL lipids may play a critical role in mediating many of these events (3–7). Diabetic vascular disease may similarly result from covalent modification of vascular wall and plasma proteins by glucose, which in its open chain form possesses a reactive aldehyde moiety (8–10).

Despite widespread interest in the potential importance of reactive aldehydes in the pathogenesis of disease and aging (3–12), little is known regarding the nature of the covalent adducts formed between aldehydes and proteins in vivo. Most studies have relied on immunohistochemical methods to detect aldehyde-modified proteins (13–16), and the exact structure(s) of the cognate epitope(s) generally is unknown. Indeed, the only well-characterized products of the reaction of aldehydes with proteins in vivo are glucoselysine (17), fructoselysine (the Amadori product; ref. 17), pentosidine (18) and $N^\epsilon$-(carboxymethyl)lysine (19), which are generated in vitro by the reaction of reducing sugars with proteins.

A potential pathway proposed and considered herein for vascular injury involves myeloperoxidase, a heme protein secreted by phagocytes (7, 20–22). Myeloperoxidase uses $H_2O_2$ generated by phagocytes to produce diffusible cytotoxic oxidants (23–28). Immunohisto-chemical and biochemical studies have demonstrated that active myeloperoxidase is a component of human atherosclerotic lesions (22). The patterns of immunostaining for the enzyme (22) and protein-bound lipid oxidation products in atherosclerotic lesions (15) are remarkably similar.

The best characterized product of myeloperoxidase is hypochlorous acid (HOCl), which is generated from chloride ion ($Cl^-$) in a two electron oxidation reaction (Equation 1; refs. 21,23).

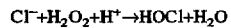

$$Cl^- + H_2O_2 + H^+ \rightarrow HOCl + H_2O \qquad \text{(Equation 1)}$$

HOCl bleaches heme proteins (30), converts amines to chloramines (31–33), inactivates sulfhydryl groups (34,35) and chlorinates unsaturated lipids (36–38).

Another substrate for oxidation by myeloperoxidase is L-tyrosine, which undergoes a one electron oxidation reaction to form tyrosyl radical (25,26). Tyrosyl radical converts protein-bound tyrosyl residues to o,o'-dityrosine and initiates lipid peroxidation, which may render LDL atherogenic (25,26,39,40).

It has been recently demonstrated that activated phagocytes also employ the myeloperoxidase-$H_2O_2$-$Cl^-$ system to convert L-tyrosine to the amphipathic aldehyde, p-hydroxyphenylacetaldehyde (pHA) (27). At physiological concentrations of L-tyrosine and $Cl^-$, PHA is the major product of phagocyte activation (27).

BRIEF DESCRIPTION OF THE INVENTION

In accordance with the present invention a diagnostic method and screening test for atherosclerosis and analogous diseases involving activated phagocytes and/or inflammation is provided.

The method comprises determining the presence of p-hydroxyphenylacetaldehyde-lysine (pHA-lysine) as a highly selective and sensitive marker for myeloperoxidase-mediated oxidative damage in a body fluid or tissue.

Detection of pHA-lysine in the body fluid or tissue of a patient at a level which is substantially elevated relative to the level in a normal patient thereby is useful for screening for atherosclerosis and a wide variety of diseases involving activated phagocytes and/or inflammation.

The diagnostic method also is useful as an assay for oxidative stress in vivo and for monitoring the effectiveness of therapeutic intervention for atherosclerosis and analogous diseases involving activated phagocytes and/or inflammation.

The body fluid or tissue for the use in the diagnostic method can be, e.g., blood serum or plasma, urine or body tissues or cells containing metabolic products of activated phagocytes.

In accordance with the invention, it has been found that pHA, the major product of L-tyrosine oxidation by phagocytes, reacts with the free amino group of lysine residues on proteins to form a Schiff base (See Scheme I, below). The structure of the reduced protein adduct was established unambiguously as pHA-lysine by mass spectrometric analysis and high resolution NMR spectroscopy. Moreover, pHA-lysine was detected in human inflammatory tissues, demonstrating that pHA modifies proteins in vivo.

pHA-Lysine was also generated in model proteins exposed to synthetically prepared pHA, L-tyrosine oxidized by the myeloperoxidase-$H_2O_2$-$Cl^-$ system, and L-tyrosine oxidized by activated human phagocytes. These results indicate free pHA generation by myeloperoxidase as a critical step in the reaction pathway. Consistent with these findings, addition of the $H_2O_2$ scavenger catalase, and the peroxidase inhibitors azide and cyanide, inhibited pHA-lysine generation by both the purified enzymatic system and activated human neutrophils.

Covalent modification of lysine residues on intracellular and membrane-associated proteins of intact neutrophils and erythrocytes was observed following pHA synthesis by myeloperoxidase. Thus, production of pHA at sites of inflammation results in the covalent modification of extracellular, membranous and intracellular target proteins.

pHA-Lysine was the major adduct detected in the amino acid hydrolysates of model proteins exposed to pHA, reduced with $NaCNBH_3$, and subjected to acid hydrolysis. Detection of pHA-lysine within human tissue thus serves as a highly selective and sensitive marker for myeloperoxidase-mediated oxidative damage, as in atherosclerosis. The stable isotope dilution GC-MS assay developed herein is capable of detecting pHA-lysine at the femtomole level, confirming its utility for assessing the degree of protein modification by phagocyte-generated aldehydes in a variety of inflammatory disease states.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the accompanying drawings in which, briefly:

BRIEF DESCRIPTION OF THE DRAWINGS

FIG. 2 shows in two parts, FIGS. 2A and 2B, negative-ion chemical ionization-gas chromatography-mass spectrum of the reduced Schiff base formed between pHA and $N^\alpha$-acetyl-lysine. The major product of the reaction between $N^\alpha$-acetyl-lysine and pHA (FIG. 1, retention time 14.0 min) was isolated by reverse phase HPLC, and its n-propyl ester, per-PFP derivative subjected to GC-MS analysis as described under "Methods."

The gas chromatographic separation was carried out on a 15 m DB-5 capillary column (J & W Scientific; 0.35 mm i.d., 1.0 μm film thickness) run with the following temperature gradient: 60° C. to 150° C. at 60° C./min, then 150° C. to 250° C. at 10° C./min. Injector, transfer line, and source temperatures set at 250° C., 250° C. and 150° C., respectively.

Figure 3:
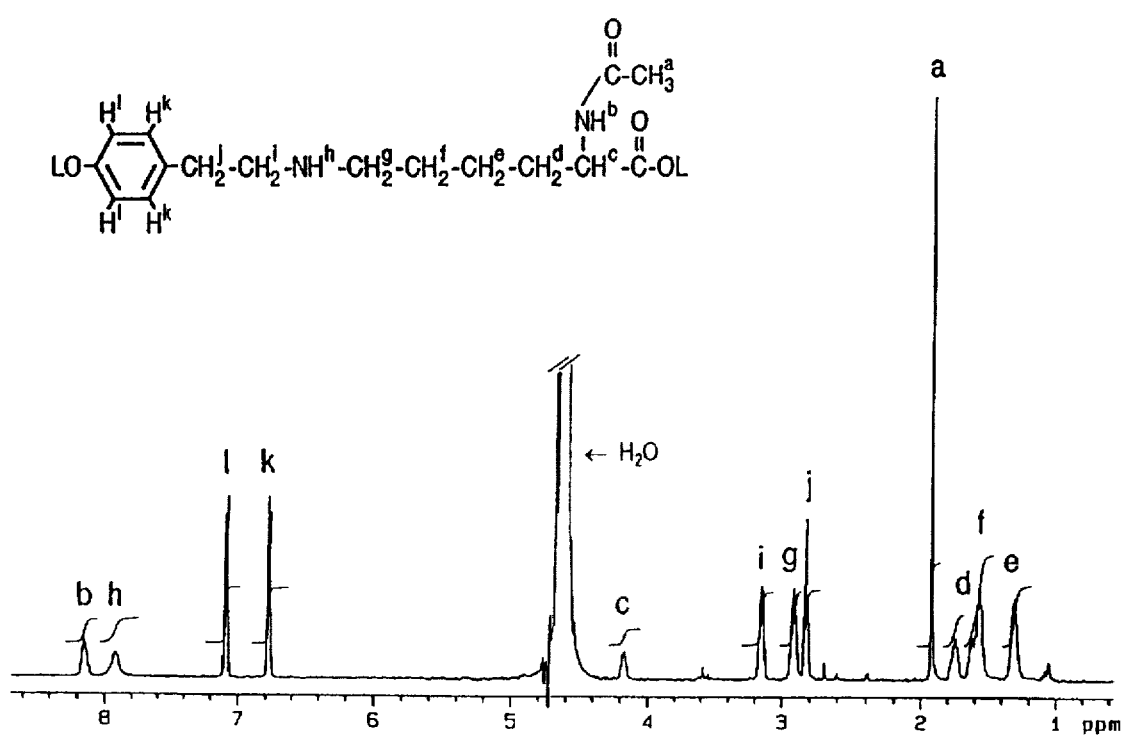

FIG. 3. shows $^1$H NMR spectrum of the reduced Schiff base formed between pHA and $N^\alpha$-acetyl-lysine. The major product of $N^\alpha$-acetyl-lysine and pHA (FIG. 1, retention time 14.0 min) was isolated by reverse phase HPLC and analyzed by $^1$H NMR as described under "Methods." Peak assignments established by TOCSY (FIG. 4) are depicted (Inset) and relative integrated areas are indicated. The integrated areas of the α-proton and amide ($N^\alpha$ and $N^\epsilon$) protons are <1 due to partial suppression and saturation transfer from exchanging water (which was irradiated prior to signal excitation), respectively.

The protons assigned as "d" are not degenerate, and one resonates very close to the methylene (f) signals. At neutral pH, protons adjacent to the amides show coupling to nearby methylene groups but not to the amide protons, which exchange rapidly with solvent. Upon addition of DCl the amide exchange was slowed (permitting detection of the amide protons), leading to broadening of resonances adjacent to the amides. Protons not observed due to rapid exchange with solvent are designated (L).

Figure 4:
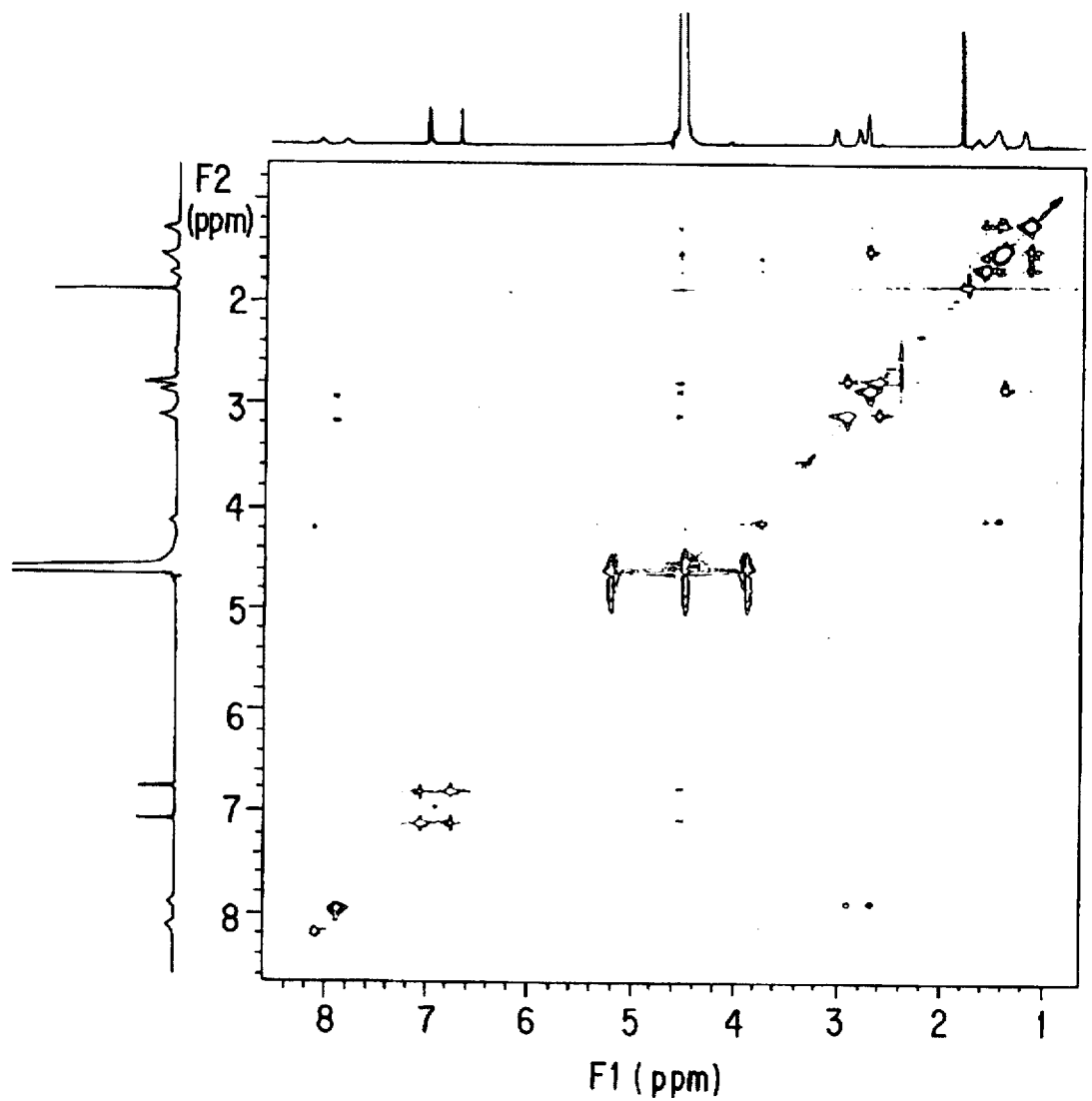

FIG. 4 shows two dimensional total correlation spectrum of $N^\alpha$-acetyl-$N^\epsilon$-pHA-lysine. The sample used for this spectrum was identical to that in FIG. 3. Cross peaks permit the assignment of resonances of the reduced Schiff base (FIG. 3). Artifacts near 4.7 ppm in F1 and F2 arise from the intense water signal.

Figure 5:
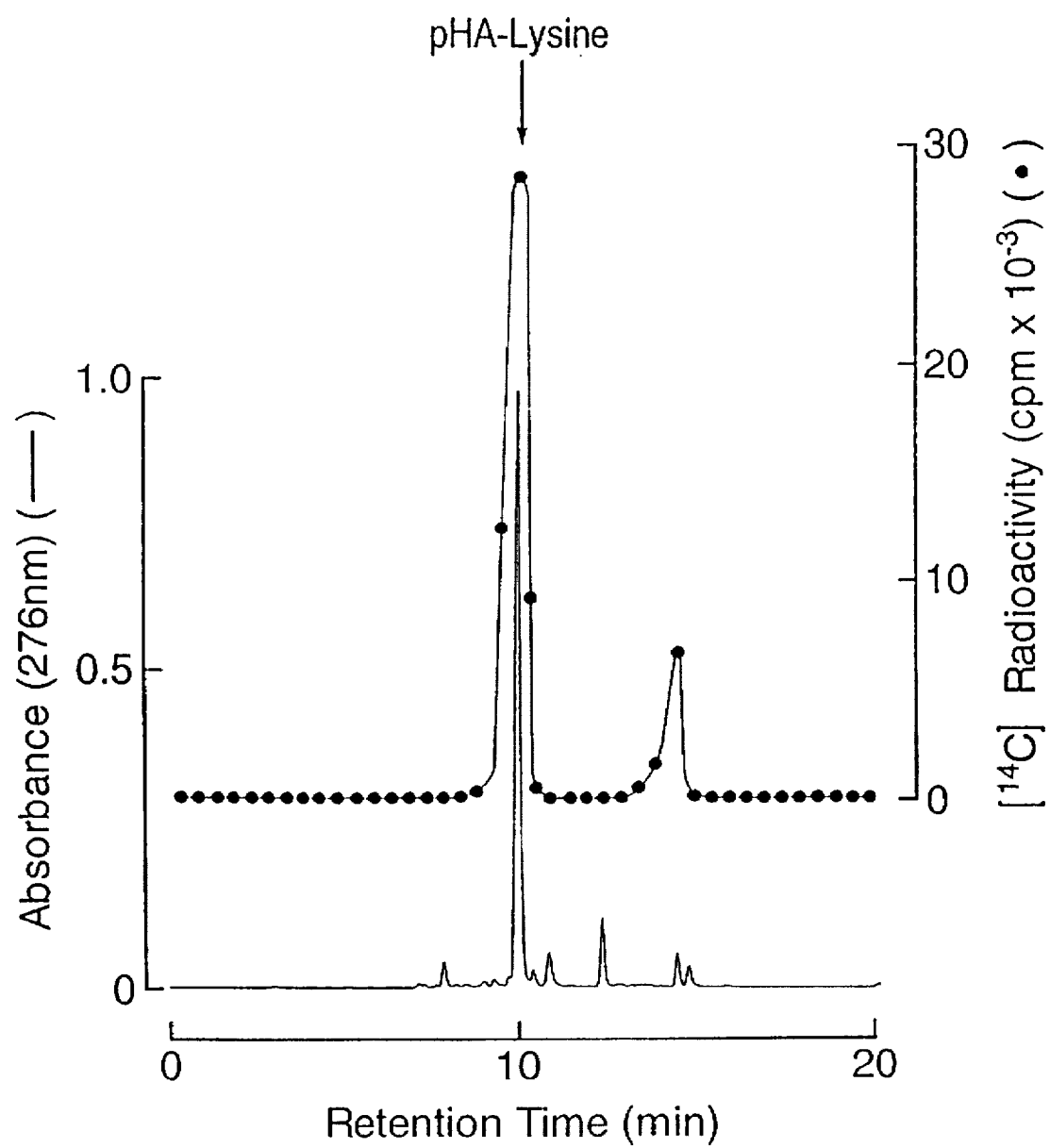

FIG. 5 shows reverse phase HPLC analysis of BSA reacted with radiolabeled pHA. BSA (1 mg/ml) was incubated at 37° C. for 2 h with purified [$^{14}$C]pHA (1.0 mM) in Buffer B (20 mM sodium phosphate, 100 μM DTPA, pH 7.0). Reaction products were reduced by addition of 10 mM $NaCNBH_3$, incubation at 37° C. for 1 h, and modified BSA was then precipitated with 10% trichloroacetic acid at 0° C.

The pellet was washed twice with ice-cold 10% trichloroacetic acid and subsequently hydrolyzed with HBr as described under "Methods." The amino acid hydrolysate was subjected to reverse-phase HPLC employing a linear gradient of 0–100% methanol in 0.1% TFA (pH 2.5) over 25 min at 1 ml/min. Fractions were dried and analyzed by scintillation spectrometry. The identity of the major radioactive compound as pHA-lysine was confirmed by GC-MS analysis. Note that L-tyrosine derived from BSA co-elutes with pHA-lysine under these HPLC conditions and contributes to the absorbance at $A_{276\ nm}$.

Figure 6A:
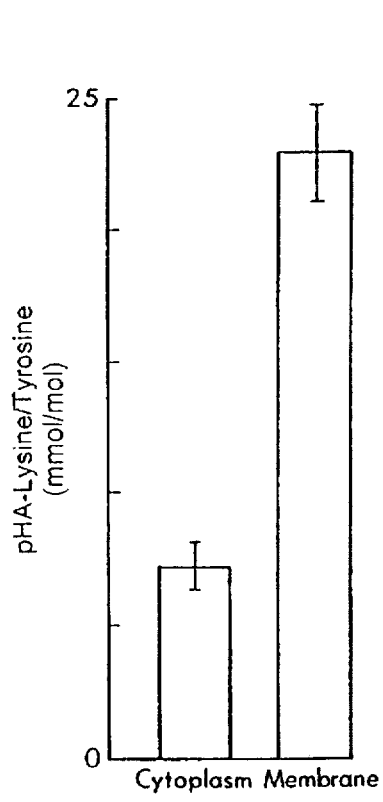
Figure 6B:
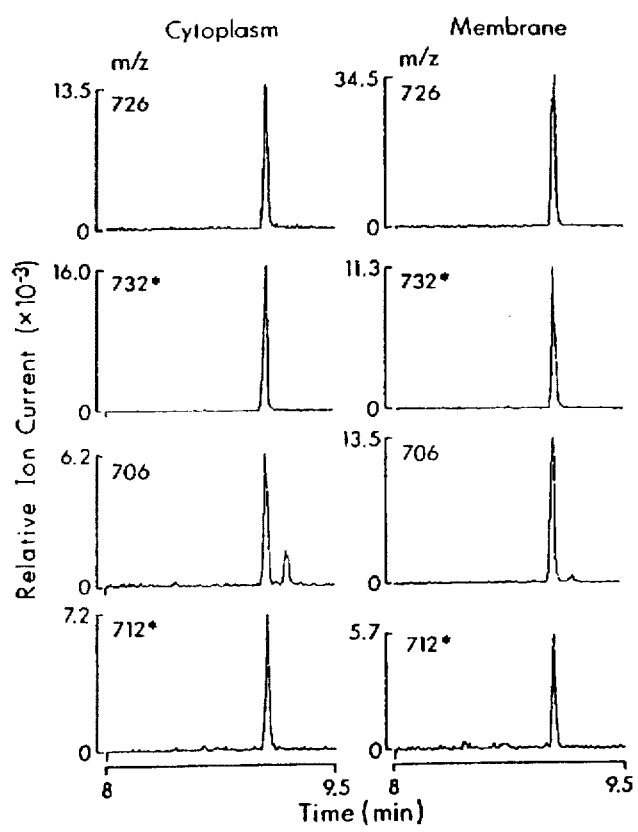

FIG. 6 shows in two parts, FIG. 6A and FIG. 6B, quantification of pHA-lysine in cytoplasmic and membrane-associated proteins of red blood cells exposed to the myeloperoxidase-$H_2O_2$-$Cl^-$-tyrosine system. Red blood cells from whole blood ($1 \times 10^6$/ml) were incubated with myeloperoxidase (40 nM), $H_2O_2$ (100 μM), 100 mM $Cl^-$, and L-tyrosine (100 μM) for 1 h at 37° C. in Medium B. Following reduction with $NaCNBH_3$, erythrocyte cytosolic and membrane-associated proteins were isolated by ultracentrifugation as described under "Methods."

(FIG. 6A): The content of pHA-lysine in erythrocyte cytoplasmic and membrane-associated proteins was determined by stable isotope dilution GC-MS. Values represent the mean ± SEM for three independent determinations.

(FIG. 6B): Selected ion monitoring of the base peak (m/z 726; $M^-$-HF) and another major fragment ion (m/z 706; $M^-$-2HF) of pHA-lysine from erythrocyte cytoplasmic and membrane-associated proteins exposed to myeloperoxidase-generated pHA.

Gas chromatographic separations were performed on a 12 m HP-1 capillary column (Hewlett Packard; 0.20 mm i.d., 0.33 μm film thickness) run with the following temperature gradient: 70° C. to 200° C. at 60° C./min; then 200° C. to 270° C. at 10° C./min. Injector, transfer line, and source temperatures set at 250° C., 250° C. and 180° C., respectively. *Ions arising from [$^{13}C_6$]-labeled pHA-lysine internal standard.

Figure 7:
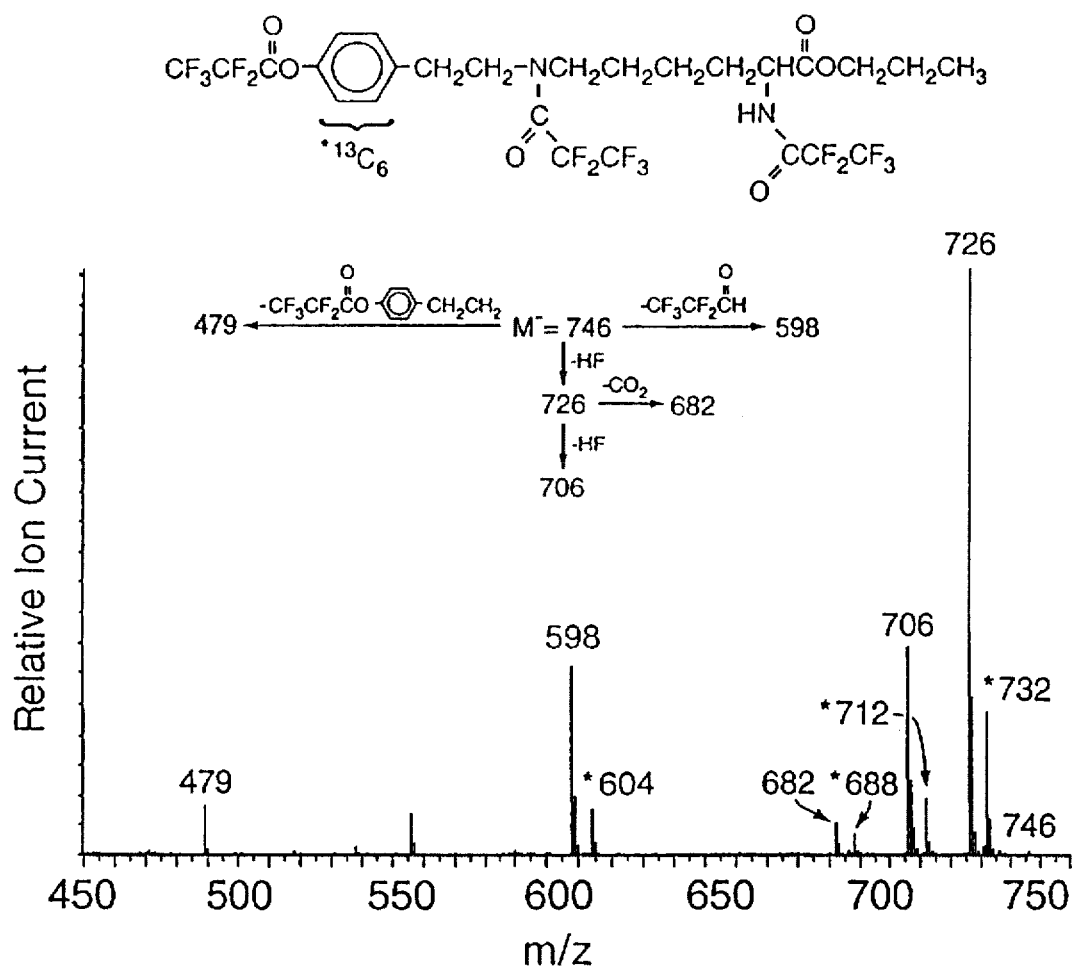

FIG. 7 shows pHA-Lysine formation in BSA exposed to activated human neutrophils. Freshly harvested human neutrophils ($1 \times 10^6$/ml) were incubated in Medium A supplemented with BSA (1 mg/ml) and L-tyrosine (100 μM). Cells were stimulated with phorbol myristate acetate (200 nM), incubated at 37° C. for 2 h, and reduced with $NaCNBH_3$ (10 mM final) at 37° C. for 2 h. Neutrophils were removed by centrifugation.

Protein in the supernatant was precipitated at 0° C. with 10% trichloroacetic acid, acid hydrolyzed, and the amino acid hydrolysate was subjected to GC-MS. The negative-ion chemical ionization mass spectrum and proposed fragmentation pattern of the n-propyl ester, per PFP derivative of pHA-lysine are illustrated. *Ions arising from [$^{13}C_6$]-labeled pHA-lysine internal standard.

Figure 8:
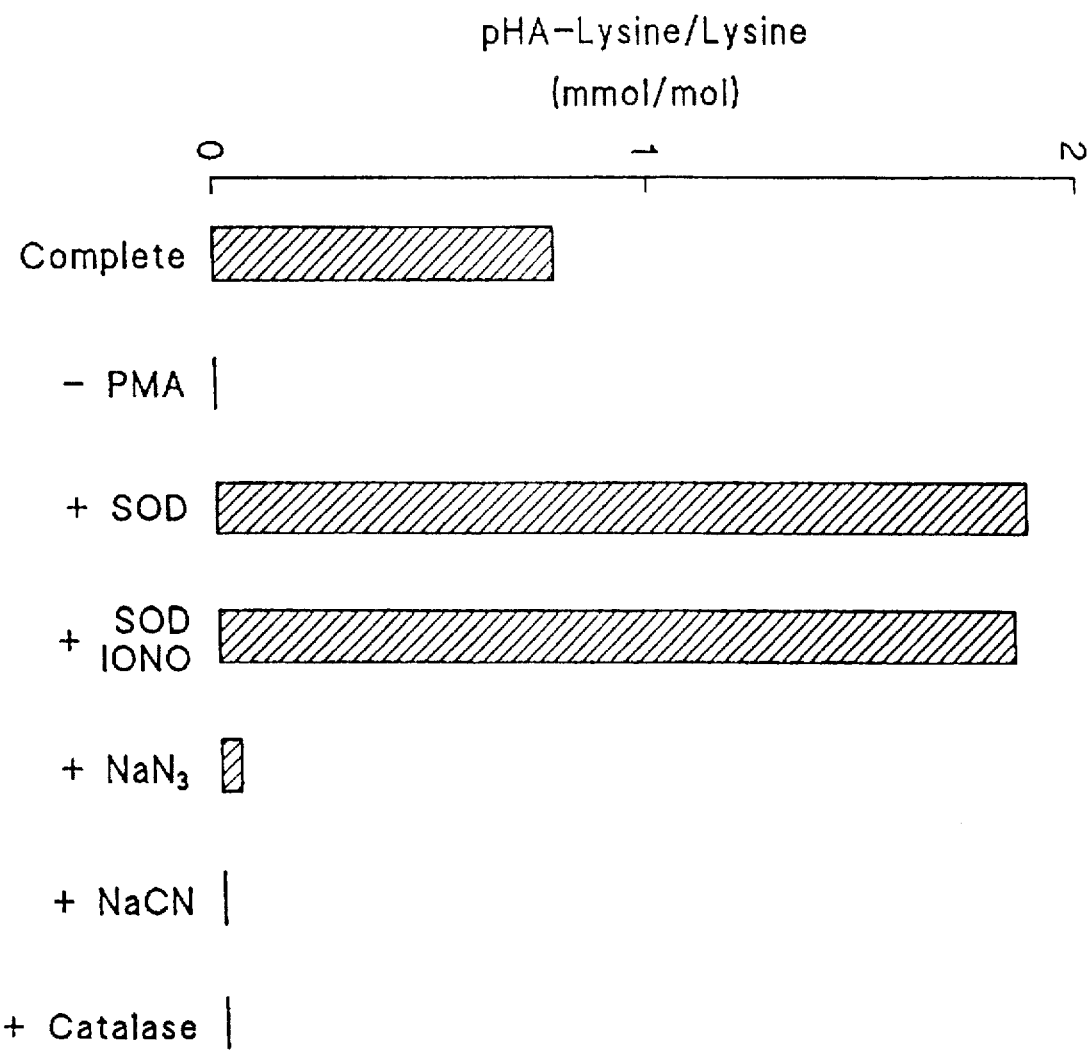

FIG. 8 shows formation of pHA-lysine in endogenous proteins of activated human neutrophils. The complete system (Complete) consisted of freshly harvested human neutrophils ($1 \times 10^6$/ml) incubated in Medium A supplemented with 200 μM L-tyrosine and 200 nM phorbol myristate acetate (PMA). Cells were pelleted after a 60 min incubation at 37° C. Neutrophil proteins were reduced with 10 mM $NaCNBH_3$ for 2 h at 37° C., and subjected to acid hydrolysis. The content of pHA-lysine in the amino acid hydrolysate was determined by stable isotope dilution GC-MS. Where indicated, superoxide dismutase (SOD; 10 μg/ml), ionomycin antibiotic (IONO; 1 μM), $NaN_3$ (1 mM), NaCN (1 mM) or catalase (20 μg/ml) were included with the complete system.

Figure 9:
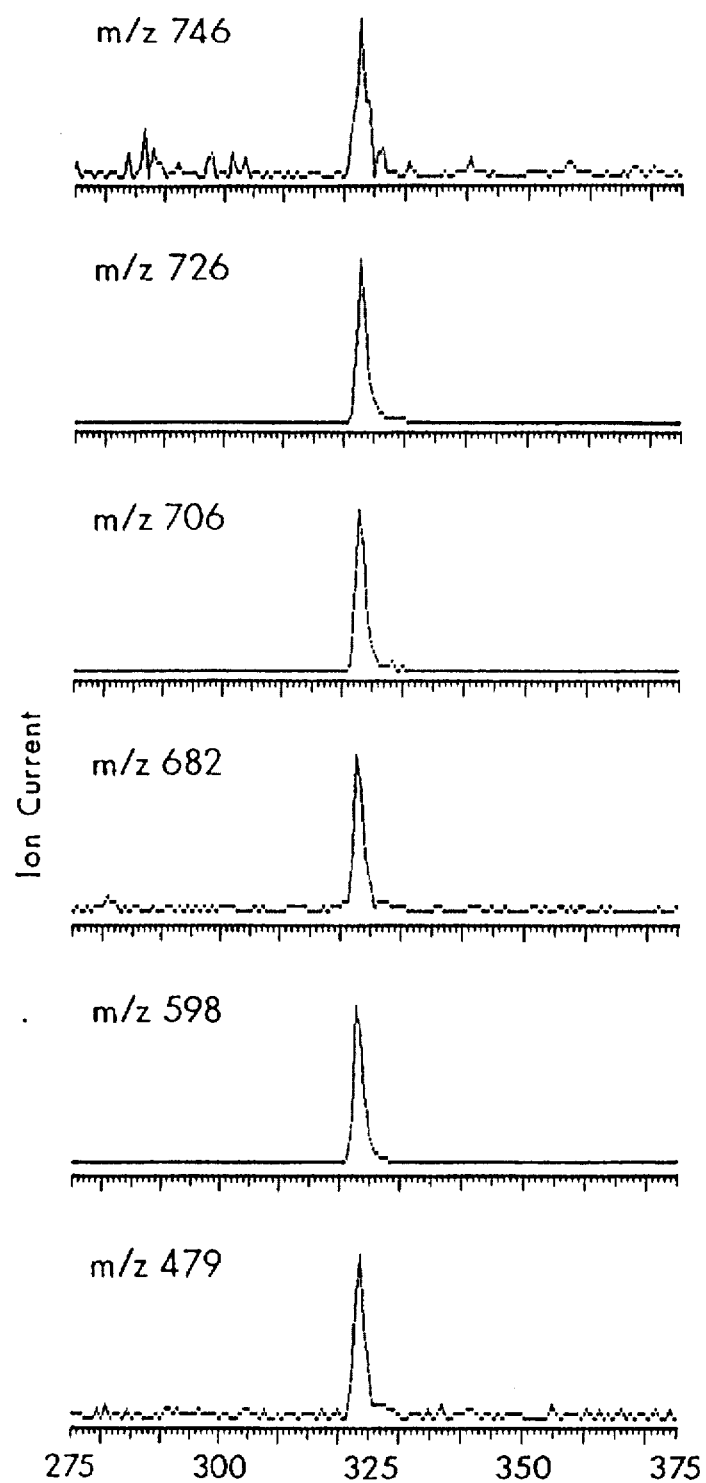

FIG. 9 shows mass spectrometric detection of pHA-lysine in human inflammatory tissue. Fluid from an intra-abdominal abscess was collected and mixed 1:1 (v:v) with ice-cold Buffer B supplemented with catalase and sodium azide, and then immediately immersed in ice-cold water. The sample was reduced by 10 mM $NaCNBH_3$ in the presence of 100 mM ammonium acetate, delipidated, and $^{13}$C-labelled pHA-lysine internal standard was added.

The proteins were acid hydrolyzed, isolated using a C18 reverse phase column, and derivatized for selected ion monitoring GC-MS analysis as described under "Methods." Ions from the n-propyl-per PFP derivative of pHA-lysine were monitored at m/z 746 ($M^-$), 726 ($M^-$-HF), 706 ($M^-$-2HF), 682 ($M^-$-HF—$CO_2$), 598 ($M^-$-$CF_3CF_2CHO$) and 479 ($M^-$-$CF_3CF_2COO$—$C_6H_4$—$CH_2CH_2$).

The retention time of the ions were identical to the corresponding ions derived from [$^{13}C_6$]-labeled pHA-lysine internal standard. Gas chromatographic separations were carried out on a 30 m DB-17 capillary column (J & W Scientific; 0.25 mm i.d., 0.25 μm film thickness) run with the following temperature gradient: μm film thickness) run with the following temperature gradient: 175° C. for 3 min, then 175° C. to 270° C. at 40° C./min. Injector, transfer line, and source temperatures set at 250° C., 250° C. and 120° C., respectively.

In order to further illustrate the invention in greater detail, the following Examples were carried out although it will be appreciated that the invention is not limited to these specific examples or the details described therein.

EXAMPLES

Materials $D_2O$, L-[$^{13}C_6$]lysine and L-[$^{13}C_6$]tyrosine were purchased from Cambridge Isotopes, Inc. L-[$^{14}$C]Tyrosine was purchased from Dupont-New England Nuclear. HPLC solvents were purchased from Baxter. Chelex-100 resin, fatty acid-free BSA and crystalline catalase (from bovine liver; thymol-free) were purchased from Boehringer-Mannheim. Sodium phosphate, ethyl acetate, $H_2O_2$ and NaOCl were purchased from Fisher Chemical Company. All other materials were purchased from Sigma Chemical Company except where indicated.

Methods

General Procedures—Myeloperoxidase (donor:hydrogen peroxide, oxidoreductase, EC 1.11.1.7) was isolated ($A_{430\ nm}/A_{280\ nm}$ ratio of 0.6) and stored as previously described (25,41).

Enzyme concentration was determined spectrophotometrically ($\epsilon_{430}$=170 $mM^{-1}cm^{-1}$; ref. 42). Human neutrophils were isolated by buoyant density centrifugation (27). Cell experiments were performed in Medium A (Hank's Balance Salt Solution (magnesium-, calcium-, phenol-, and bicarbonate-free; pH 7.2; Gibco-BRL) supplemented with 100 μM diethylenetriaminepentaacetic acid (DTPA)).

For neutrophil experiments, ionomycin and phorbol myristate acetate were added from concentrated stocks in ethanol or dimethylsulfoxide, respectively; the final content of each vehicle was ≦0.2% (v/v).

HOCl concentration was determined spectrophotometrically ($\epsilon_{292}$=350 $M^{-1}cm^{-1}$; ref. 43).

Buffers were Chelex-100 treated and supplemented with 100 μM DTPA to remove redox-active metals.

Sodium dodecyl sulfate-polyacrylamide gel electrophoresis (SDS-PAGE) was performed as described by Laemmli (44).

Protein content was measured by the method of Lowry, et al. (45) with bovine serum albumin as the standard.

Amino acid analyses were performed at the Washington University School of Medicine Protein Chemistry Core Laboratory. Pre-column derivatization of amino acid hydrolysates with 6-aminoquinoyl-N-hydroxy-succinimidyl carbamate was followed by high performance liquid chromatography (HPLC) with uv detection (46,47).

Synthesis of pHA—NaOCl (1:1, mol:mol) was added drop-wise to L-tyrosine (2 mM in 20 mM sodium phosphate, pH 7.0) with constant mixing at 0° C. The solution was then warmed to 37° C. for 60 min and immediately used for experiments. Preparations were analyzed by reverse phase HPLC prior to use and routinely were ≥95% pure.

High Performance Liquid Chromatography—HPLC analysis of pHA was performed utilizing a C18 column (Beckman µporacil, 5 µm resin, 4.6 mm×260 mm) equilibrated with solvent A (5% methanol, 0.1% trifluoroacetic acid, (TFA), pH 2.5).

Products were monitored by absorbance ($A_{276\ nm}$) and eluted at a flow rate of 1 ml/min with a nonlinear gradient generated with solvent B (90% methanol, 0.1% TFA, pH 2.5) as follows:

0% to 35% solvent B over 10 min;

isocratic elution at 35% solvent B for 20 min;

12% to 100% B over 10 min.

[$^{14}$C]pHA-lysine was quantified by scintillation spectrometry following isolation on reverse phase HPLC (Table I, below) with the following gradient:

0% to 10% solvent B over 5 min;

isocratic elution at 10% B for 20 min;

10% to 100% solvent B over 10 min.

Under these conditions, pHA-lysine is base-line resolved from tyrosine.

Generation of pHA-Lysine Adduct—Reactions were carried out for 4 h at 37° C. under the reaction conditions indicated in the Brief Description of the Figures, above. Schiff base adducts then were reduced by addition of 10 mM NaCNBH$_3$ and incubation overnight or for the indicated time at 37° C. Where indicated, 100 mM ammonium acetate was included during reduction to scavenge free pHA.

pHA-Lysine Formation on Membrane-Associated and Cytoplasmic Proteins of Intact Cells. Whole blood diluted with Medium B (10 mM phosphate buffered saline, pH 7.0 (Sigma Chemical Company) supplemented with 100 µM DTPA) to a final concentration of 1×10$^6$ erythrocytes/ml was incubated with myeloperoxidase (40 nM), H$_2$O$_2$ (100 µM) and L-tyrosine (100 µM) for 1 h at 37° C.

Schiff base adducts were reduced by incubation at 37° C. for 2 h with 10 mM NaCNBH$_3$ in the presence of 100 mM ammonium acetate. Cells were pelleted by centrifugation (5000×g) for 15 min at 4° C., washed twice with Medium B, and then homogenized on ice with a tight fitting Potter-Elvejheim homogenizer.

The cell lysate was fractionated into soluble and membrane-associated fractions by ultracentrifugation (100,000×g for 1 h at 4° C.), delipidated with two sequential extractions with water-washed diethyl ether (1:1; v:v), and L-[$^{13}$C$_6$]tyrosine (300 nmol; a marker of protein content) and N$^α$-acetyl-N$^ε$-[$^{13}$C$_6$]pHA-lysine (20 pmol) added as internal standards. Following HBr hydrolysis and solid phase extraction on a C18 Supelco column, the content of pHA-lysine was determined by stable isotope dilution GC-MS as described below.

Figure 1:
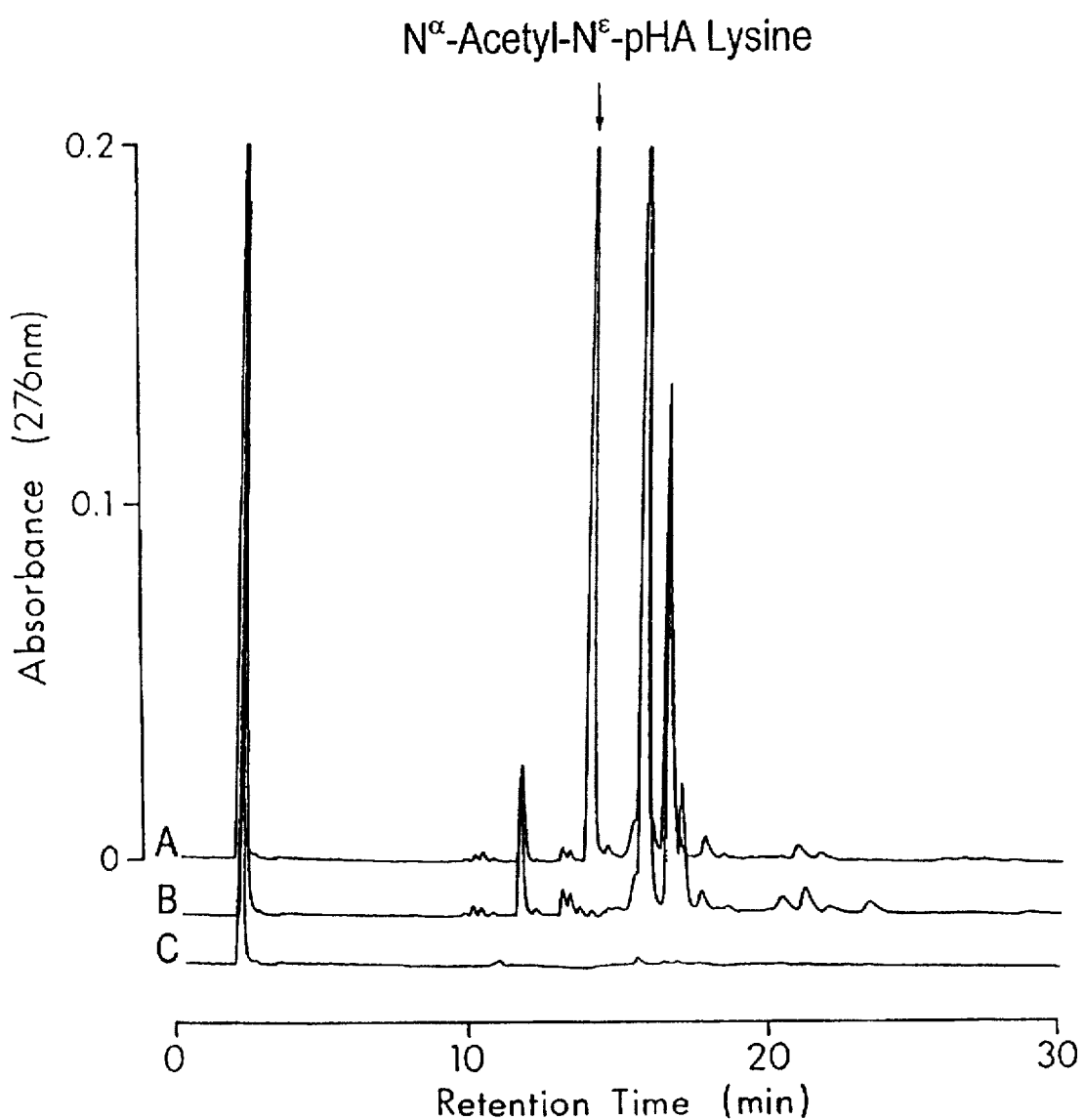
FIG. 1 shows reverse-phase HPLC detection of the reduced Schiff base adduct formed in the reaction between pHA and $N^\alpha$-acetyl-lysine. Reactions containing both pHA (2 mM) and $N^\alpha$-acetyl-lysine (4 mM) or either component alone were incubated for 4 h at 37° C. in 20 mM sodium phosphate, 100 μm DTPA, pH 7.4. $NaCNBH_3$ (10 mM) was then added and reaction mixtures incubated at 37° C. overnight. Products were subjected to HPLC analysis on a C18 column as described under "Methods", below. The single major acid-stable compound formed in the presence of both pHA and $N^\alpha$-acetyl-lysine (retention time 14.0 min) was collected and identified as $N^\alpha$-acetyl-$N^\epsilon$-pHA-lysine in the tests described in FIGS. 2–4.

Preparation of N$^α$-acetyl-N$^ε$-[$^{13}$C$_6$]pHA-Lysine Internal Standard—L-[$^{13}$C$_6$]tyrosine (2 mM) in 20 mM sodium phosphate (pH 7.0) was first converted to [$^{13}$C$_6$]pHA (24 98% purity as assessed by reverse phase HPLC) by addition of NaOCl as described above. N$^α$-Acetyl-lysine (4 mM) was then added, the mixture was incubated at 37° C. for 4 h, and the Schiff base was reduced by overnight incubation with 10 mM NaCNBH$_3$. N$^α$-Acetyl-N$^ε$-[$^{13}$C$_6$]pHA-lysine was isolated by reverse phase HPLC (FIG. 1).

Protein Hydrolysis—Solutions of proteins covalently modified by pHA were dried under vacuum. Known quantities of either L-[$^{13}$C$_6$]lysine or L-[$^{13}$C$_6$]tyrosine and N$^α$-acetyl-N$^ε$-[$^{13}$C$_6$]pHA-lysine were then added as internal standards. HBr (6N, 0.5 ml) supplemented with phenol (1%) was added to the sample (250 µg protein) in glass 2 ml reaction vials equipped with Mininert gas-tight valves and the samples were alternately evacuated and purged with argon gas five times. The argon-covered solution was hydrolyzed at 120° C. for 24 h. The protein hydrolysate was diluted to 2.0 ml with 0.1% TFA and applied to a C18 column (Supleclean, 3 ml, Supelco Co.) equilibrated with 0.1% TFA. Following a 2 ml wash with 0.1% TFA, pHA-lysine was recovered with 2 ml of 20% methanol in 0.1% TFA.

Samples were evaporated to dryness under either anhydrous N$_2$ or vacuum prior to derivatization. n-Propyl esters were prepared by the addition of 200 µl 3.5 M HBr in n-propanol (Cambridge Isotope Laboratories) followed by heating at 65° C. for 30 min. Propylated products were dried under N$_2$ and pentafluoropropionyl (PFP) derivatives were then generated by addition of excess pentafluoropropionic acid anhydride (Pierce Chemical Co.) in ethyl acetate (1:3; v:v) for 1 h at 65° C. Heptafluorobutyryl (HFB) derivatives of esterified reaction products were prepared by addition of 50 µl ethyl acetate/heptafluorobutyric acid anhydride (4:1; v/v) and heating at 65° C. for 30 min.

Tissue Collection—Samples were immersed in ice and processed within 30 min of collection. Schiff bases were rendered acid stable by reduction with 10 mM NaCNBH$_3$ in the presence of 100 mM ammonium acetate (to scavenge any free aldehyde), 1 mM NaN$_3$ (a myeloperoxidase inhibitor) and 300 nM catalase (a H$_2$O$_2$ scavenger) in 50 mM sodium phosphate (pH 7.4) at 37° C. for 1 h. Preliminary experiments confirmed that no additional pHA-lysine was generated under these conditions when samples were supplemented with myeloperoxidase (20 nM) and H$_2$O$_2$ (100 µM).

Samples were subsequently delipidated, the protein pellet washed twice with 10% trichloroacetic acid at 0° C. under a fume hood, and then subjected to acid hydrolysis, solid phase extraction on a C18 minicolumn, and derivatization for GC-MS analysis.

Mass Spectrometric Analysis—Amino acids were quantified using stable isotope dilution GC-MS in the negative-ion chemical ionization mode. Samples were analyzed with a Hewlett Packard 5890 gas chromatograph interfaced with a Hewlett Packard 5988A mass spectrometer with extended mass range. Gas chromatographic separations were typically carried out utilizing a 12 m HP-1 capillary column (Hewlett Packard; 0.2 mm i.d., 0.33 µm film thickness) in the splitless mode with He as the carrier gas. Unless otherwise indicated, the column was run with the following temperature gradient: 70° C. to 200° C. at 60° C./min, followed by 200° C. to 250° C. at 10° C./min. Injector, transfer line and source temperatures were set at 250° C., 250° C., and 150° C., respectively. High resolution mass spectrometry with a VG-ZAB SE double-focusing mass spectrometer was performed to confirm the proposed structural assignments of major ions by determining their elemental composition. The resolution was set at 10,000 with perfluorokerosine as the reference.

Amino acids were quantified as their n-propyl, per-PFP derivative using selected ion monitoring. pHA-Lysine was monitored using the base peak at m/z 726 (M$^-$-HF), another major fragment ion at m/z 706 (M$^-$-2HF), and their corresponding isotopically labeled internal standard ions at m/z 732 and m/z 712. L-tyrosine was monitored using the base peak at m/z 367 (M$^-$-PFP), another major fragment ion at m/z 495 (M$^-$-HF), and their corresponding isotopically labeled internal standard ions at m/z 373 and m/z 501. L-Lysine was monitored using the base peak at m/z 460 (M$^-$-HF), another major fragment ion at m/z 440 (M$^-$-2HF), and their corresponding isotopically labeled internal standard ions at m/z 466 and m/z 446.

Quantification was based on an external calibration curve constructed with each authentic compound and its isotopically labeled internal standard. To ensure that no interfering ions were co-eluting with the analyte, the ratio of ion currents of the two characteristic ions of each compound and its internal standard were routinely monitored. All amino acids were baseline separated and co-eluted with $^{13}$C-labeled internal standards. The limit of detection (signal/noise >10) was <1 pmol for all compounds.

NMR Studies—Analyses were performed at 25° C. in D$_2$O:H$_2$O (1:9; v:v) with HPLC purified N$^\alpha$-acetyl-N$^\epsilon$-pHA-lysine using a Varian Unity-Plus 500 spectrometer (499.843 MHz for $^1$H) equipped with a Nalorac indirect detection probe. $^1$H chemical shifts were referenced to external sodium 3-(trimethylsilyl)-propionate-2,2,3,3,d$_4$ in D$_2$O.

Prior to NMR analysis, the sample of N$^\alpha$-acetyl-N$^\epsilon$-pHA-lysine was acidified with DCl (Cambridge Isotopes Inc.) until inhibition of amide proton exchange was observed. For proton and total correlation spectroscopy (TOCSY) experiments, the intense water signal was attenuated by transmitter pre-irradiation. The proton NMR spectrum of N$^\alpha$-acetyl-N$^\epsilon$-pHA-lysine was recorded at 25° C. from 64 transients under the following conditions: pre-acquisition delay=2 s, acquisition time=1.89 s (37,760 complex data points), pulse width=7 μs (80° flip angle) and spectral width=10,000 Hz. The free induction decay was processed with a line broadening apodization of 1.0 Hz. For TOCSY, eight transients were collected for each of 200 t$_1$ domain increments. A 10 ms mixing period was employed resulting in cross peaks for only the strongest scalar couplings (geminal and vicinal). The acquisition time was 0.256 s in t$_2$ (2048 complex data points) and 0.050 s in t$_1$ (200 data points). TOCSY data was processed by the hypercomplex method with Gausian weighting in both t$_1$ and t$_2$ dimensions. Digital signal processing was employed to suppress artifacts arising from the intense water resonance.

RESULTS pHA forms a Schiff base adduct with the free amino group of N$^\alpha$-acetyl-lysine.

Initially, a study was made of the reaction of pHA with N$^\alpha$-acetyl-lysine, a model compound for free amino groups on proteins, to facilitate the isolation and characterization of products. Reactions were carried out at pH 7.4 and 37° C. in a phosphate-buffered physiological salt solution.

Reverse phase HPLC analysis of the complete reaction mixture after reduction with NaCNBH$_3$ revealed a single major acid-stable product (FIG. 1; retention time 14.0 min). Formation of the compound required the presence of both pHA and N$^\alpha$-acetyl-lysine (FIG. 1); it was undetectable in the absence of reduction under the acidic conditions employed for HPLC analysis.

Characterization of the stable reduced product by NMR and GC-MS (see below) demonstrated that it was N$^\alpha$-acetyl-N$^\epsilon$-pHA-lysine (Scheme I). The failure to detect the compound in the presence of acid suggested that the initial reaction of the aldehyde and the free amino group of N$^\alpha$-acetyl-lysine resulted in formation of a Schiff base. Reduction of the Schiff base would then yield the acid-stable aldehyde-lysine adduct (Scheme I).

Figures 2A, 2B:
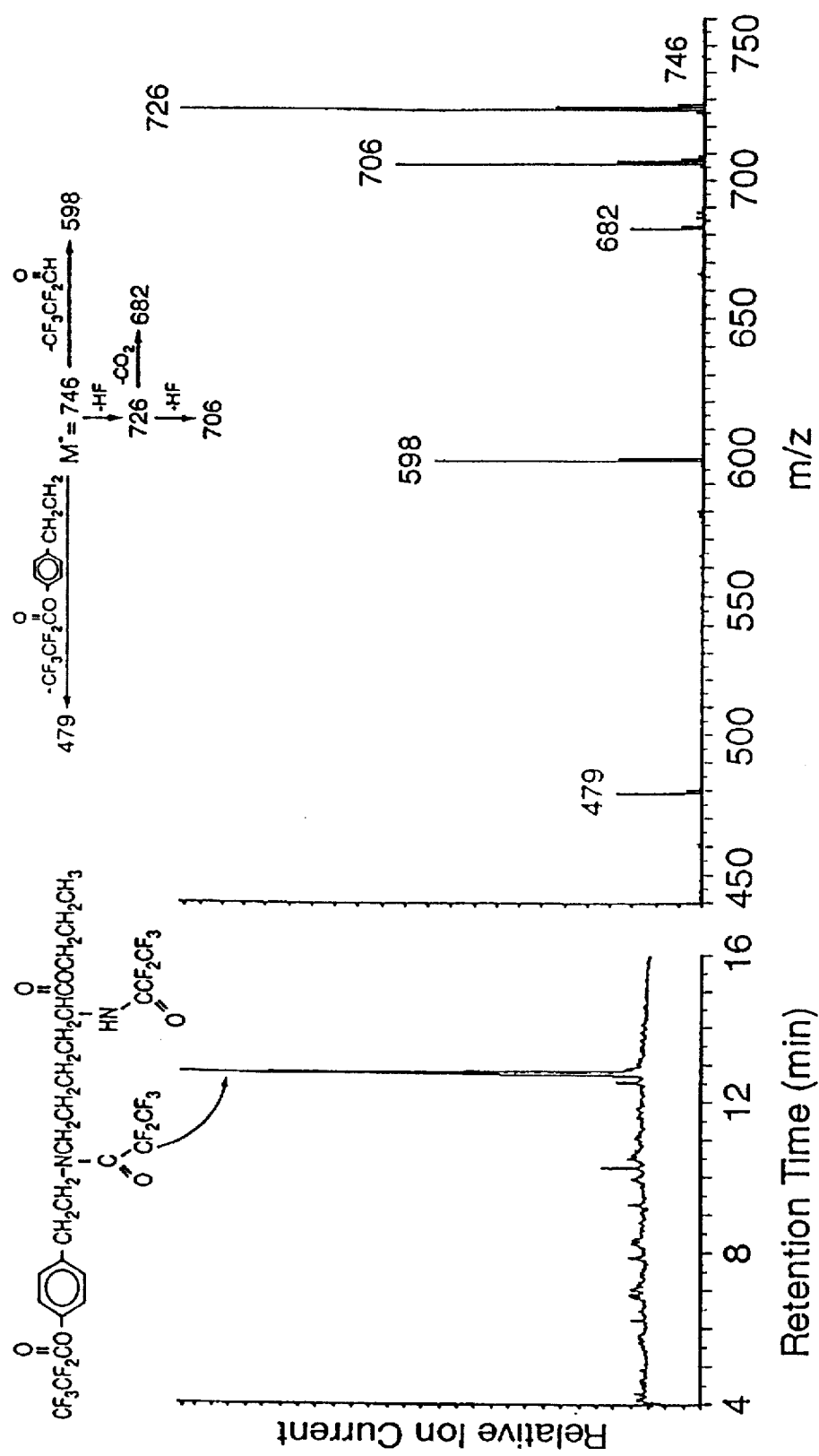
(FIG. 2A) Total ion chromatogram of the derivatized HPLC-purified product.
(FIG. 2B) Negative-ion chemical ionization mass spectrum of the derivatized HPLC-purified product. The mass spectrum is consistent with the proposed structure (Inset, FIG. 2B) and fragmentation pattern (Inset, FIG. 2A) of the n-propyl ester, per-PFP derivative of $N^\alpha$-acetyl-$N^\epsilon$-pHA-lysine.

To determine the structure of the compound, the reaction mixture was reduced with NaCNBH$_3$, and HPLC purified material was derivatized and subjected to GC-MS analysis. A single major peak of material was apparent in the total ion chromatogram (FIG. 2A). The negative-ion chemical ionization mass spectrum of the n-propyl ester, per-PFP derivative of the compound (FIG. 2B) was consistent with the proposed structure of pHA-lysine (FIG. 2A, Inset).

The compound demonstrated a low abundance ion on selected-ion monitoring at m/z 746, the anticipated m/z of the molecular ion (M$^-$), that co-eluted with the major ions seen in the mass spectrum of the compound. GC-MS analysis of the n-propyl ester, per-HFB derivative of the compound also exhibited a mass spectrum consistent with the proposed structure; ions were observed at m/z 896 (M$^-$), 876 (M$^-$-HF), 856 (M$^-$-2HF), 832 (M$^-$-HF—CO$_2$), 698 (M$^-$-CF$_3$CF$_2$CF$_2$CHO) and 579 (M$^-$-CF$_3$CF$_2$COO—C$_6$H$_4$—CH$_2$CH$_2$).

NMR spectroscopy was performed to establish unambiguously the structure of the compound (FIG. 3). Both the chemical shifts and integrated peak areas of the $^1$H NMR spectrum were consistent with the structure of pHA-lysine (FIG. 3, Inset). To confirm the proton assignments, TOCSY was employed to identify scalar couplings between resonances (FIG. 4). The sequential order of 2,3-bond H-H couplings observed in the TOCSY experiment established the structure of the compound as N$^\alpha$-acetyl-N$^\epsilon$-pHA-lysine. Collectively, these studies indicate that pHA forms a Schiff base with the free amino group of N$^\alpha$-acetyl-lysine, and that the structure of the stable reduction product is N$^\alpha$-acetyl-N$^\epsilon$-pHA-lysine (Scheme I).

pHA generated by the myeloperoxidase-H$_2$O$_2$—Cl$^-$ system covalently modifies lysine residues of BSA.

Preliminary experiments utilizing L-[$^{14}$C]tyrosine demonstrated that bovine serum albumin (BSA) was covalently modified by a L-tyrosine-derived product in the presence of the complete myeloperoxidase-H$_2$O$_2$-Cl$^-$ system, as assessed by SDS-PAGE and subsequent auto-radiography.

To determine whether the Schiff base adduct between pHA and the ε-amino group of lysine accounted in part for this reaction, BSA was exposed to the myeloperoxidase-H$_2$O$_2$ system supplemented with physiological concentrations(48) of $^{14}$C-labelled L-tyrosine (100 μM) and chloride (100 mM).

Following incubation, the protein was reduced with NaCNBH$_3$, and the content of [$^{14}$C]pHA-lysine was determined by reverse phase HPLC and scintillation counting as described under "Methods." In the presence of the complete myeloperoxidase-H$_2$O$_2$—Cl$^-$ system, lysine residues of BSA were converted to pHA-lysine (Table I). Synthesis of the adduct required for the presence of myeloperoxidase, H$_2$O$_2$, L-tyrosine and Cl$^-$, and was inhibited by the H$_2$O$_2$ scavenger catalase (Table I). Addition of either azide or cyanide, two heme protein inhibitors, resulted in inhibition of pHA-lysine synthesis, consistent with the reaction being dependent upon peroxidase.

The Cl$^1$-dependence of the enzymatic reaction suggested that HOCl (or perhaps enzyme-bound hypochlorite; refs.

49,50) was an intermediate in the formation of pHA 27. Consonant with this proposal, addition of HOCl and L-tyrosine to BSA resulted in the covalent modification of $N^\epsilon$-lysine residues (Table I). Furthermore, both lactoperoxidase and horseradish peroxidase, which do not use chloride as substrate (23), failed to generate either pHA (27) or the lysine adduct (Table I). The covalent modification of BSA by pHA was independent of free metal ions because all reactions were carried out in the presence of DTPA, a potent inhibitor of metal-catalyzed reactions.

The major covalent adduct generated between pHA and BSA is pHA-lysine.

To determine the quantitative significance of pHA-lysine relative to other potential protein adducts, BSA was incubated with HPLC purified $^{14}C$-labelled pHA. The modified protein was then incubated with $NaCNBH_3$ hydrolyzed in HBr, and the amino acid hydrolysate analyzed by reverse-phase HPLC and scintillation spectrometry. Over 80% of the radioactivity recovered in the amino acid hydrolysate co-chromatographed with authentic pHA-lysine (FIG. 5). The identity of the radiolabeled compound as pHA-lysine was confirmed by GC-MS analysis.

Amino acid analysis confirmed that lysine was the major target for covalent modification by pHA. Incubation of BSA with purified pHA in the presence of $NaCNBH_3$ resulted in the consumption of 34% of total L-lysine residues in the protein. Small but consistent losses of L-arginine (~6%) were also observed, and may account for the late eluting product seen in FIG. 5. There were also small but consistent losses (~3%) in L-aspartic acid, suggesting a reaction involving the free amino group of the N-terminal aspartic acid of BSA.

Schiff bases are in equilibrium with their parent aldehyde and amino moieties. In the presence of $NaCNBH_3$, the formation of pHA-lysine is enhanced by the reduction of existing Schiff bases. To estimate the number of protein lysine residues modified in the absence of a reducing agent, BSA was incubated with pHA, and then the Schiff base adduct was stabilized by reduction with $NaCNBH_3$ in the presence of high concentrations of ammonium acetate (to scavenge unreacted pHA). Amino acid hydrolysis confirmed that lysine was the major target for covalent modification by pHA under these conditions (Table II). The loss of L-lysine residues was accounted for by the appearance of a novel product which coeluted with L-glycine on amino acid analysis, and that is believed to represent pHA-lysine.

pHA, an amphipathic L-tyrosine oxidation product, covalently modifies both inteqral membrane and cytoplasmic proteins of intact cells.

Previous studies revealed that ~90% of the pHA generated by activated neutrophils partitioned into the membrane fraction due to the amphipathic nature of the aldehyde (27). It was therefore determined herein whether myeloperoxidase-generated pHA could covalently modify membrane-associated and cytoplasmic proteins of intact cells. Red blood cells were incubated with myeloperoxidase, $H_2O_2$ and physiological concentrations of L-tyrosine and $Cl^-$, and the extent of pHA-lysine formation was determined.

Substantial amounts of the Schiff base adduct between pHA and $N^\epsilon$-lysine residues were generated on both membranous and cytoplasmic proteins as detected by GC-MS (FIG. 6A). Selected ion monitoring GC-MS analysis demonstrated that the major ions expected for pHA-lysine co-eluted with those of synthetically prepared $[^{13}C_6]$pHA-lysine (FIG. 6B).

Generation of pHA-lysine required myeloperoxidase, $H_2O_2$, L-tyrosine, and red blood cells. These results indicate that pHA readily diffuses through plasma membranes to react with intracellular proteins. The relative enrichment of pHA-lysine in membrane-associated proteins may be due either to high local concentrations of pHA or their location at the interface between the intracellular milieu and extracellular space where free pHA is generated initially by myeloperoxidase.

pHA generated by human neutrophils forms pHA-lysine adducts on model proteins.

Phorbol ester-activated human neutrophils incubated in a balanced salt solution supplemented with BSA and plasma concentrations of L-tyrosine generated pHA-lysine as determined by stable isotope dilution GC-MS (FIG. 7 and Table III). Selected ion monitoring GC-MS confirmed the presence of pHA-lysine, revealing ions with the expected retention time and m/z found in synthetically prepared $[^{13}C_6]$ pHA-lysine. Moreover, the negative-ion chemical ionization mass spectrum of the neutrophil product was identical to that of authentic pHA-lysine (compare FIG. 7 and FIG. 2B).

Covalent modification of lysine residues in BSA by neutrophil-generated pHA required cells, L-tyrosine, and an activating stimulus (Table III). Addition of superoxide dismutase to the reaction mixture, which accelerates the conversion of superoxide anion into $H_2O_2$ 500-fold at neutral pH (51), caused a 2-fold increase in the yield of the adduct (Table III). Addition of the calcium ionophore ionomycin, which promotes pHA synthesis (27), also resulted in additional pHA-lysine generation, consistent with enhanced $H_2O_2$ synthesis and/or myeloperoxidase degranulation.

Generation of the covalent adduct by activated human neutrophils was sensitive to inhibition by catalase, indicating that $H_2O_2$ was required for pHA-lysine synthesis. The heme poisons azide and cyanide inhibited pHA-lysine formation, consistent with a role of myeloperoxidase in aldehyde generation by the cells (27). Collectively, these results herein indicate that activated human neutrophils employ the myeloperoxidase-$H_2O_2$—$Cl^-$ system to generate pHA, which then reacts with the free amino groups of proteins to form pHA-lysine.

Activated neutrophils form pHA-lysine adducts on endogenous proteins.

Activation of human neutrophils with phorbol ester in medium containing physiological concentrations of L-tyrosine resulted in the covalent modification of neutrophil proteins (FIG. 8). As with BSA, the cell-mediated reaction was stimulated by superoxide dismutase, and inhibited by either peroxidase inhibitors ($NaN_3$ and $NaCN$) or an $H_2O_2$ scavenger (catalase). (FIG. 8).

pHA-Lysine is present in human inflammatory tissues.

To explore the role of pHA in protein modification in vivo, a variety of acute inflammatory tissues were examined for the presence of the lysine adduct. Specimens were reduced with $NaCNBH_3$ in the presence of excess ammonium acetate (to scavenge free aldehyde), $NaN_3$ (a myeloperoxidase inhibitor) and catalase (a $H_2O_2$ scavenger). Samples were subsequently delipidated, subjected to acid hydrolysis, and analyzed by GC-MS. pHA-Lysine was readily detected by selected ion monitoring in fluid isolated from an intra-abdominal abscess (FIG. 9). Similar results were obtained with specimens collected from a gouty knee and an infected pilonidal cyst.

Scheme I

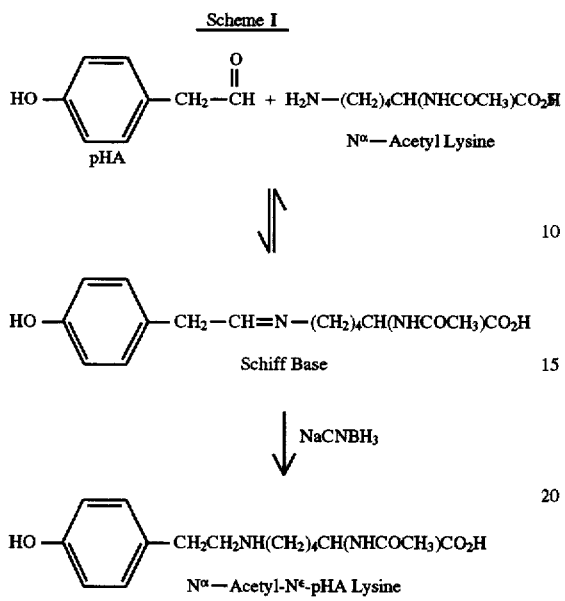

TABLE I

Covalent Modification of BSA Lysine Residues by the Myeloperoxidase-$H_2O_2$—Cl-Tyrosine System

| Condition | pHA-Lysine nmol |
|---|---|
| Complete System: | |
| BSA + MPO + $H_2O_2$ + L-Tyrosine + Cl | 7.3* |
| Complete System Minus: | |
| MPO | 0 |
| $H_2O_2$ | 0 |
| L-Tyrosine | 0 |
| Cl | 0 |
| Complete System Plus: | |
| Catalase (10 μg/ml) | 0 |
| $NaN_3$ (1 mM) | 0 |
| NaCN (1 mM) | 0 |
| BSA + HOCl + L-Tyrosine + Cl | 15.8** |
| BSA + Lactoperoxidase + $H_2O_2$ + L-Tyrosine + Cl | 0 |
| BSA + Horseradish peroxidase + $H_2O_2$ + L-Tyrosine + Cl | 0 |

The complete system consisted of Buffer B (20 mM sodium phosphate, pH 7.0, 100 μM DTPA) supplemented wtih BSA (1 mg/ml), myeloperoxidase (MPO; 40 nM), $H_2O_2$ (100 μM), L-[$^{14}$C]tyrosine (100 μM) and NaCl (100 mM). Where indicated, lactoperoxidase (100 μg/ml) and horseradish peroxidase (10 μg/ml) were substituted for myeloperoxidase, or reagent HOCl (100 μM) replaced myeloperoxidase and $H_2O_2$. After a 1 h incubation at 37° C., reaction products were reduced with $NaCNBH_3$. BSA precipitated and the pellet washed (×3) with 10% trichloroacetic acid, and then acid hydrolyzed. The pHA-lysine content of the amino acid hydrolysate was then determined by reverse phase HPLC and scintillation counting as described under "Methods." Product identity was confirmed by GC-MS analysis. *2.5% of the $H_2O_2$ in the complete system and **5.5% of reagent HOCl was used for the generation of pHA-lysine.

TABLE II

Amino Acid Composition Analysis of BSA Modified by Myeloperoxidase-Generated pHA

| Amino Acid | % Native BSA |
|---|---|
| Alanine | 100 |
| Arginine | 101 |
| Aspartate/Asparagine | 99 |
| Glutamate/Glutamine | 100 |
| Glycine* | 145* |
| Histidine | 103 |
| Isoleucine | 100 |
| Leucine | 100 |
| Lysine | 82 |
| Phenylalanine | 101 |
| Proline | 100 |
| Serine | 101 |
| Threonine | 97 |
| Tyrosine | 98 |
| Valine | 99 |

BSA (1 mg/ml) was incubated overnight at 37° C. with pHA (1 mM) in Medium B. The reaction was terminated by the addition of 10 mM $NaCNBH_3$ and 100 mM ammonium acetate (to reduce Schiff bases and scavenge free pHA, respectively). After a 2 h incubation at 37° C., modified protein was isolated by size exclusion chromatography using a DG-10 column (Bio-Rad) equilibrated with $H_2O$. The protein was then dried under vacuum, acid hydrolyzed and subjected to amino acid analysis as described under "Methods." Cysteine, methionine and tryptophan are acid-labile and were not quantified.

*Represents the combined yield of glycine and the presumed pHA-lysine adduct.

TABLE III

Covalent Modification of the Lysine Residues of BSA by Activated Human Neutrophils

| Condition | pHA-Lysine/Lysine (μmol/mol) |
|---|---|
| Complete System: | |
| Cells + L-Tyrosine + BSA + PMA | 297 |
| Complete System Minus: | |
| Cells | <0.01 |
| L-Tyrosine | <0.01 |
| PMA | <0.01 |
| Complete System Plus: | |
| SOD (10 μg/ml) | 545 |
| SOD (10 μg/ml) + Ionomycin(1 μM) | 696 |
| Catalase (200 μg/ml) | 8 |
| $NaN_3$ (1 mM) | 40 |
| NaCN (1 mM) | 14 |

Human neutrophils (1×10⁶/ml) were incubated for 2 h at 37° C. in Hank's Balanced Salt Solution supplemented with DTPA (100 μM) and BSA (1 mg/ml). Neutrophils were activated with phorbol ester (PMA; 200 nM) and maintained in suspension by intermittent inversion (Complete System). Neutrophils were removed by centrifugation, and Schiff bases in the supernatant reduced by addition of $NaCNBH_3$ (10 mM) and ammonium acetate (100 mM). After a 2 h incubation at 37° C., protein in the supernatant was precipitated with ice-cold 10% trichloroacetic acid, and the protein pellet was subjected to acid hydrolysis. The pHA-lysine content of the amino acid hydrolysate was determined by stable isotope dilution GC-MS. SOD, superoxide dismutase.

Various other examples will be apparent to the person skilled in the art after reading the present disclosure without departing from the spirit and scope of the invention. It is intended that all such other examples be included within the scope of the appended claims. Thus, the presence and level of the pHA-lysine in the sample of body fluid or tissue also can be determined by immunoprecipitation procedures in an immunoassay with polyclonal or monoclonal antibodies to the pHA-lysine. One- and two-site radioimmunoassays and enzyme immunoassays, e.g., an enzyme-linked immunosorbent assay (ELISA) procedure as described by Engvall and Perlmann, *J. Immunol.* 109, 129–135 (1972), can be used in the diagnostic method of the invention. Monoclonal antibodies for use in such procedures can be prepared by conventional hybridoma methodology as described by Köhler and Milstein, *Nature* 256, 495–497 (1975), and *Eur. J. Immunol.* 6, 511–519 (1976); and Goding, *Monoclonal Antibodies: Principles and Practice*, Academic Press Inc., New York, 1983).

REFERENCES

1. Brown, M. S. and Goldstein, J. L. (1986) *Science* 232, 34–47
2. Kannel, W. B. and McGee, D. L. (1979) *Circulation* 59, 8–13
3. Esterbauer, H., Schaur, R. J. and Zollner, H. (1991) *Free Rad Biol. & Med.* 11, 81–128
4. Witztum, J. L. and Steinberg, D. (1991) *J. Clin. Invest.* 88, 1785–1792
5. Witz, G. (1989) *Free Rad. Biol. & Med.* 7, 333–349
6. Esterbauer, H., Gebicki, J., Puhl, H. and Jurgens, G. (1992) *Free Rad. Biol. Med* 13, 341–390
7. Berliner, J. A. and Heinecke, J. W. (1996) *Free Rad. Biol. & Med.* 20,707–727
8. Baynes, J. W. (1991) *Diabetes* 40, 405–412
9. Brownlee, M. (1991) *Ann. Rev. Med.* 42, 159–166
10. Bucala, R. and Cerami, A. (1992) *Adv. Pharm.* 23, 1–34
11. Stadtman, E. R. (1992) *Science* 257, 1220–1224
12. Lieber, C. S. (1994) *Annals of Medicine* 26, 325–330
13. Haberland, M. E., Cheng, L. and Fong, D. (1988) *Science* 241,215–218.
14. Steinbrecher, U. P., Lougheed, M., Kwan, W. C. and Dirks, M. (1989) *J. Biol. Chem.* 264, 15216–15223
15. Rosenfeld, M. E., Palinski, W., Ylä-Herttuala, S., Butler, S. and Witztum, J. L. (1990) *Arterio.* 10, 336–349
16. Uchida, K., Toyokuni, S., Nishikawa, K., Oda, H., Hiai, H., and Stadtman, E. R. (1994) *Biochemistry* 33, 12487–12494
17. Ledl, F. and Schleicher, E. (1990) *Angew. Chem. Int. Ed. Engl.* 29, 565–594
18. Sell, D. R. and Monnier, V. M. (1989) *J. Biol. Chem.* 264, 21597–21602
19. Ahmed, M. U., Thorpe, S. R. and Baynes, J. W. (1986) *J. Biol. Chem* 261, 4889–4894
20. Agner, K. (1972) in *Structure and Function of Oxidation-Reduction Enzymes* Akeson, A. and Ehrenberg, A., Eds.) pp. 329–335, Pergamon Press, New York
21. Klebanoff, S. J. and Clark, R. A. (1978) in *The Neutrophil: Function and Clinical Disorders* pp. 447–451, Elsevier/North Holland Biomedical Press, Amsterdam
22. Daugherty, A., Dunn, J. L. Rateri, D. L. and Heinecke, J. W. (1994) *J. Clin. Invest.* 94,437–444
23. Harrison, J. E. and Schultz, J. (1976) *J. Biol. Chem.* 251, 1371–1374
24. Foote, C. S., Goyne, T. E. and Lehrer, R. I. (1981) *Nature* 301,715–716
25. Heinecke, J. W., Li, W., Daehnke, H. L. and Goldstein, J. A. (1993) *J. Biol. Chem.* 268, 4069–4077
26. Heinecke, J. W., Li, W., Francis, G. A. and. Goldstein, J. A. (1993) *J. Clin. Invest.* 91,2866–2872
27. Hazen, S. L., Hsu, F. F. and Heinecke, J. W. (1996) *J. Biol. Chem.* 271, 1861–1867
28. Hazen, S. L., Hsu, F. F., Mueller, D. M., Crowley, J. R. and Heinecke, J. W., (1996) *J. Clin. Invest.* (In Press)
29. Hazell, L. J., Arnold, L., Flowers, D., Waeg, D., Malle, E. and Stocker, R. (1996) *J. Clin. Invest* 97, 1535–1544
30. Albrich, J. M., McCarthy, C. A. and Hurst, J. K. (1981) *Proc. Natl. Acad. Sci. USA* 78, 210–214
31. Weil, I. and Morris, J. C. (1949) *J Amer. Chem. Soc.* 71, 1664–1671
32. Thomas, E. L., Jefferson, M. M. and Grisham, M. B. (1982) *Biochem.* 21, 6299–6308
33. Weiss, S. J., Klein, R., Slivka, A. and Wei, M., (1982). *J. Clin. Invest.* 70, 598–607
34. Knox, W. E., Stumpf, P. K., Green, D. E. and Auerbach, V. H. (1948). *J. Bact.* 55, 451458
35. Test, S. T. and Weiss, S. J. (1986) *Adv. Free Rad. Biol. Med.* 2, 91–116
36. Winterbourn, C. C., VandenBerg, J. J. M., Roitman, E. and Kuypers, F. A. (1992) *Arch. Biochem. Biophys.* 296, 547–555
37. Heinecke, J. W., Li, W., Mueller, D. M., Boher, A. and Turk, J. (1994) *Biochem.* 33, 10127–10136
38. Hazen, S. L., Hsu, F. F., Duffin, K. and Heinecke, J. W. (1996) *J. Biol. Chem.* (In Press)
39. Francis, G. A., Mendez, A. J., Bierman E. L. and Heinecke, J. W. (1993) *Proc. Natl. Acad. Sci. U.S.A.* 90, 6631–6635
40. Savenkova, M. I.; Mueller D. M. and Heinecke. J. W. (1994) *J. Biol Chem.* 269, 20394–20400
41. Rakita, R. M., Michel, B. R. and Rosen, H. (1990). *Biochem.* 29, 1075–1080
42. Morita, Y., Iwamoto, H., Aibara, S., Kobayashi, T. and Hasegawa, E. (1986) *J. Biochem.* 99, 761–770
43. Morris, J. C. (1966) *J. Phys. Chem.* 70, 3798–3805
44. Laemmli, U. K. (1970) *Nature* 227, 680–685
45. Lowry, O. H., Rosenbough, N. J., Farr, A. L. and Randall, R. J. (1951) *J. Biol. Chem.* 193, 265–275
46. Cohen, S. A. and Michaud, D. P. (1993) *Anal. Biochem.* 211, 279–287
47. Liu, H. (1994) *J. Chromatog.* 670, 59–66
48. Linder, M., (1992) in *Nutritional Biochemistry and Metabolism.* Elsevier Sci. Pub. Co., Inc., New York, N.Y. p. 98
49. Hori, H., Fenna, R. E., Kimura, S. and Ikeda-Saito, M. (1994) *J. Biol. Chem.* 269, 8388–8392
50. Marquez, L. A. and Dunford, H. B. (1994) *J. Biol. Chem.* 269, 7950–7956
51. Fridovich, I. (1985) CRC Handbook of Methods: Oxygen Radical Research, R. A. Greenwald, Ed., CRC Press Inc, Boca Raton, Fla., pp213–215
52. Rhodes, J., Chen, H., Hall, S. R., Beesley, J. E., Jenkins, D. C., Collins, P. and Zheng, B. (1995) *Nature* 377, 71–75

What is claimed:

1. A diagnostic method and screening test for detection of conditions indicative of atherosclerosis and analogous diseases involving activated phagocytes and/or tissue inflammation comprising determining the presence of p-hydroxyphenylaldehyde-lysine in a test sample of a body fluid or tissue at a level which is substantially elevated relative to the level in a normal subject.

2. The method of claim 1 in which the test sample is human inflammatory tissue.

3. The method of claim 1 in which the test sample is a human blood serum or plasma fraction.

4. The method of claim 1 in which the presence and level of p-hydroxyphenylaldehyde-lysine is determined by mass spectrometric analysis and high resolution NMR spectroscopy.

5. The method of claim 1 in which the presence and level of p-hydroxyphenylaldehyde-lysine is determined by an immunoassay with antibodies to said p-hydroxyaldehyde-lysine.

* * * * *

UNITED STATES PATENT AND TRADEMARK OFFICE
CERTIFICATE OF CORRECTION

PATENT NO. : 5,731,208
DATED : MARCH 24, 1998
INVENTOR(S) : JAY W. HEINECKE

It is certified that error appears in the above-identified patent and that said Letters Patent is hereby corrected as shown below:

```
In line 5 of Claim 1 (col. 16, line 52):
"p-hydroxyphenylaldehyde-lysine" should read
--p-hydroxyphenylacetaldehyde-lysine--.
In line 2 of Claim 4 (col. 16, line 60):
"p-hydroxyphenylaldehyde-lysine" should read
--p-hydroxyphenylacetaldehyde-lysine--.
In line 2 of Claim 5 (col. 16, line 64):
"p-hydroxyphenylaldehyde-lysine" should read
--p-hydroxyphenylacetaldehyde-lysine--.
In line 4 of Claim 5 (col. 16, line 66):
"p-hydroxyaldehyde-lysine" should read
--p-hydroxyphenylacetaldehyde-lysine--.
```

Signed and Sealed this

Fourteenth Day of July, 1998

Attest:

BRUCE LEHMAN

*Attesting Officer*     *Commissioner of Patents and Trademarks*